United States Patent [19]

Sih

[11] 4,151,351

[45] Apr. 24, 1979

[54] 7,8-DIDEHYDRO-PGI$_1$ COMPOUNDS

[75] Inventor: John C. Sih, Kalamazoo, Mich.

[73] Assignee: The Upjohn Company, Kalamazoo, Mich.

[21] Appl. No.: 869,141

[22] Filed: Jan. 13, 1978

[51] Int. Cl.$^2$ .......................................... C07D 307/93
[52] U.S. Cl. ................................... 542/426; 542/429; 544/153; 544/376; 546/196; 546/256; 546/269; 546/194; 260/326.36; 260/346.22; 260/346.73; 260/239 BF
[58] Field of Search ...................... 260/346.22, 346.73; 542/426, 429

[56] References Cited

U.S. PATENT DOCUMENTS 3,954,741  5/1976  Schaaf et al. ........................ 542/426

OTHER PUBLICATIONS

Pace-Asciak et al., Prostaglandins, vol. 16, Sep. 1978, pp. 397–410.
Sih et al., Prostaglandins, vol. 16, Sep. 1978, pp. 411–416.
Pace-Asciak et al., Biochemistry, vol. 10, No. 20, 1971, pp. 3657–3663.

*Primary Examiner*—Natalie Trousof
*Assistant Examiner*—Bernard Dentz
*Attorney, Agent, or Firm*—Robert A. Armitage

[57] ABSTRACT

This invention relates to certain structural analogs of 5,6-dihydroprostacyclin (PGI$_1$) wherein an endocyclic double bond is present at the C-7 to C-8 position. These novel unsaturated prostacyclin type compounds are endoperoxide cyclooxygenase inhibitors which prevent the conversion of unsaturated fatty acids to endoperoxides (e.g., PGG$_2$ and PGH$_2$). By virtue of this pharmacological property these analogs represent potent antiinflammatory agents.

63 Claims, No Drawings

7,8-DIDEHYDRO-PGI₁ COMPOUNDS

BACKGROUND OF THE INVENTION

This invention relates to novel positional isomers of prostacyclin (PGI$_2$) and 5,6-dihydroprostacyclin (PGI$_1$). In particular, the present invention relates to prostacyclin-type compounds wherein an endocyclic double bond is present at C-7 to C-8.

Prostacyclin is an endogenously produced compound in mammalian species, being structurally and biosynthetically related to the prostaglandins (PG's). In particular, prostacyclin exhibits the following structure and atom numbering:

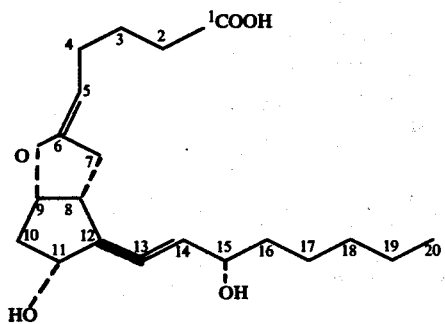

5,6-Dihydroprostacyclin exhibits the following structure and atom numbering:

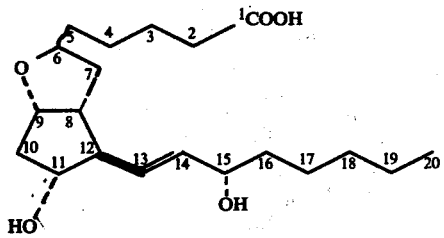

As is apparent from inspection of formulas I and II, prostacyclin and 5,6-dihydroprostacyclin (i.e., PGI$_1$) bear a structural relationship to PGF$_2\alpha$, which exhibits the following structure and atom numbering:

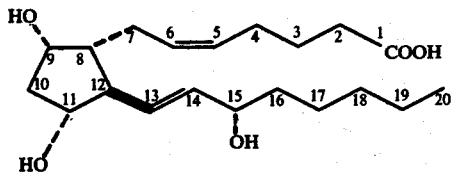

As is apparent by reference to formula III, prostacyclin and 5,6-dihydroprostacyclin may be trivially named as a derivative of PGF-type compounds. Accordingly, prostacyclin is trivially named 9-deoxy-6,9α-epoxy-(5Z)-5,6-didehydro-PGF$_1$ and 5,6-dihydroprostacyclin is named 9-deoxy-6,9α-epoxy-PGF$_1$. For description of the geometric stereoisomerism employed above, see Blackwood et al., Journal of the American Chemical Society 90, 509 (1968). Further, for a description of prostacyclin and its structural identification, see Johnson et al., Prostaglandins 12, 915 (1976).

For convenience, the novel prostacyclin analogs described herein will be referred to by the trivial, art-recognized system of nomenclature described by N. A. Nelson, Journal of Medicinal Chemistry, 17, 911 (1974) for the prostaglandins. Accordingly, all of the novel prostacyclin derivatives herein will be named either as 9-deoxy-PGF$_1$-type compounds or alternatively and preferably as PGI$_1$ or PGI$_2$ derivatives.

In formulas I and II above, as well as in formulas hereinafter, broken line attachments to any ring indicate substituents in "alpha" ($\alpha$) configuration, i.e., below the plane of such ring. Heavy solid line attachments to any ring indicate substituents in "beta" ($\beta$) configuration, i.e., above the plane of such ring. The use of wavy lines ($\sim$) herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). Also, see Nature 212, 38 (1966) for discussion of the stereochemistry of the prostaglandins, which discussion applies to the novel prostacyclin analogs herein. Expressions such as C-2, C-15, and the like, refer to the carbon atom in the prostaglandin or prostacyclin analog which is in the position corresponding to the position of the same number in PGF$_2\alpha$ or prostacyclin, as enumerated above.

With further regard to PGI$_1$, the two stereoisomeric forms thereof are depicted by the following formulas:

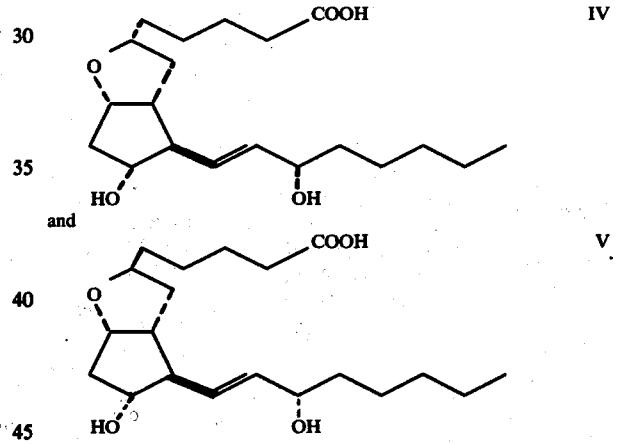

These isomeric forms, respectively referred to hereinafter as 6α-PGI$_1$ and 6β-PGI$_1$ represent the (6R) and (6S) isomers, respectively by the Cahn-Ingold-Prelog sequence rules. For convenience hereinafter the novel PGI$_1$ analogs exhibiting asymmetry at C-6 will be referred to as 6α-PGI$_1$-type or 6β-PGI$_1$-type compounds depending on whether such analogs are of the same relative stereochemical configuration as the (6R) or (6S) isomer of PGI$_1$, respectively.

Molecules of prostacyclin and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the above formula for prostacyclin corresponds to that endogeneously produced in mammalian tissues. In particular, refer to the stereoconfiguration of C-8 (alpha), C-9 (alpha), C-11 (alpha), and C-12 (beta) of the endogenously-produced prostacyclin. The mirror image of the above formula for prostacyclin represents the other enantiomer. The racemic forms of prostacyclin contains equal numbers of both enantiomeric molecules, and the above formula I and its mirror image is needed to represent correctly the corresponding racemic prostacyclin.

For convenience hereinafter, use of the term prostaglandin ("PG") or prostacyclin ("PGI$_2$") will mean the optically active form of that prostaglandin or prostacyclin thereby referred to with the same absolute configuration as PGF$_2\alpha$, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one pharmacological purpose.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostacyclin analog", as used herein, represents that stereoisomer of a prostacyclin-type product which is of the same relative stereochemical configuration as prostacyclin obtained from mammalian tissues or a mixture comprising that stereoisomer and the enantiomer thereof. In particular, where a formula is used to depict a prostacyclin-type product herein, the term "prostacyclin analog" refers to the compound of that formula or a mixture comprising that compound and the enantiomer thereof.

In addition to the above reference disclosing prostacyclin, certain positional isomers thereof have allegedly been discovered by C. Pase-Asiak and L. S. Wolfe. See for example their report in Biochem. 10:3657 (1971), purporting to describe 7,8-didehydro-PGI$_1$ and 8,9-didehydro-PGI$_1$. Further, another positional isomer of prostacyclin, trans-4,5-didehydro-PGI$_1$, has been reported by Nicolaou, et al. J.C.S. Chem. Comm-1977:331-332 and Corey, et al., J.A.C.S. 99:2006-2008 (1977). The latter two positional isomers would exhibit respectively the following structural formulas:

VI and

VII

SUMMARY OF THE INVENTION

The present invention particularly comprises: I. a prostacyclin intermediate of the formula

VIII wherein g is the integer one, 2, or 3;
wherein R$_8$ is hydrogen; hydroxy; or hydroxymethyl;
wherein Y$_1$ is
 (1) trans—CH=CH—,
 (2) cis—CH=CH—,
 (3) —CH$_2$CH$_2$—, or
 (4) —C≡C—;
wherein M$_1$ is wherein R$_5$ is hydrogen or methyl;
wherein L$_1$ is or a mixture of and wherein R$_3$ and R$_4$ are hydrogen, methyl, or fluoro, being the same or different, with the proviso that one of R$_3$ and R$_4$ is fluoro only when the other is hydrogen or fluoro; and
wherein R$_7$ is —(CH$_2$)$_m$—CH$_3$, (1)

—(CH$_2$)$_h$—〈phenyl(T)$_s$〉 (2)

—O—〈phenyl(T)$_s$〉 (3)

wherein m is the integer one to 5, inclusive, h is the integer zero to 3, inclusive; s is the integer zero, one, 2, or 3; and T is chloro, fluoro, trifluoromethyl, alkyl of one to 3 carbon atoms, inclusive, or alkoxy of one to 3 carbon atoms, inclusive, with the proviso that not more than two T's are other than alkyl; or
  II. a prostacyclin analog of the formula

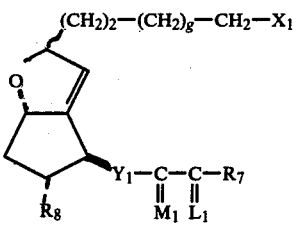

IX wherein g, R$_8$, M$_1$, Y$_1$, Z$_1$, L$_1$, and R$_7$ are as defined above; and wherein X$_1$ is (1) —COOR$_1$ wherein R$_1$ is hydrogen, alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

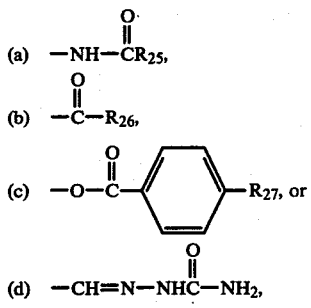

wherein R$_{25}$ is methyl, phenyl, acetamidophenyl, benzamidophenyl, or —NH$_2$; R$_{26}$ is methyl, phenyl, —NH$_2$, or methoxy; and R$_{27}$ is hydrogen or acetamido, inclusive, phenacyl, i.e.,

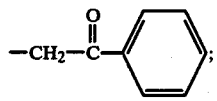

or phenacyl substituted in the para position by chloro, bromo, phenyl, or benzamido; or a pharmacologically acceptable cation; or (2) —COL$_4$, wherein L$_4$ is (a) amino of the formula —NR$_{21}$R$_{22}$; wherein R$_{21}$ and R$_{22}$ are (i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
(vii) carboxyalkyl of one to 4 carbon atoms, inclusive;
(viii) carbamoylalkyl of one to 4 carbon atoms, inclusive;
(ix) cyanoalkyl of one to 4 carbon atoms, inclusive;
(x) acetylalkyl of one to 4 carbon atoms, inclusive;
(xi) benzoylalkyl of one to 4 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of one to 4 carbon atoms, inclusive;
(xvi) pyridylalkyl substituted by one, 2, or 3 chloro, alkyl of one to 3 carbon atoms, inclusive, hydroxy, or alkoxy of one to 3 carbon atoms, inclusive;
(xvii) hydroxyalkyl of one to 4 carbon atoms, inclusive;
(xviii) dihydroxyalkyl of one to 4 carbon atoms, or
(xix) trihydroxyalkyl of one to 4 carbon atoms; with the further proviso that not more than one of R$_{21}$ and R$_{22}$ is other than hydrogen or alkyl;

(b) cycloamino selected from the group consisting of

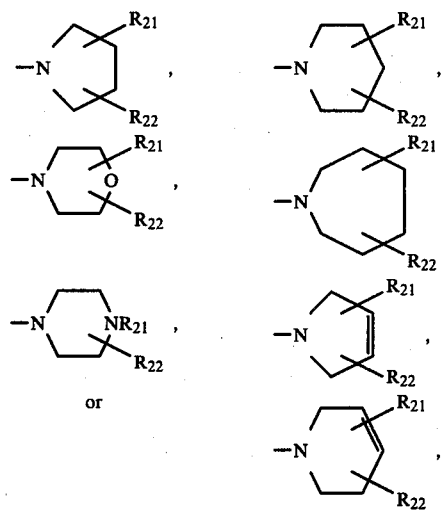

wherein R$_{21}$ and R$_{22}$ are as defined above;

(c) carbonylamino of the formula —NR$_{23}$COR$_{21}$, wherein R$_{23}$ is hydrogen or alkyl of one to 4 carbon atoms and R$_{21}$ is as defined above;

(d) sulphonylamino of the formula —NR$_{23}$SO$_2$R$_{21}$, wherein R$_{21}$ and R$_{22}$ are as defined above; or (e) hydrazino of the formula —NR$_{23}$R$_{24}$, wherein R$_{23}$ is as defined above and R$_{24}$ is amino of the formula —NR$_{21}$R$_{22}$, as defined above, or cycloamino, as defined above.

By virtue of the endocyclic unsaturation the novel compounds herein which are prostacyclin analogs or intermediates, as indicated above, are all named as 7,8-didehydro-6α- or 6β-PGI$_1$-type compounds.

When g is 2 or 3, the compounds described herein are additionally named as 2a-homo-PGI$_1$-type or 2a,2b-dihomo-PGI$_1$-type compounds, respectively. In this event the additional methylene or ethylene group is considered for the purposes of nomenclature as though it were inserted between the carbon atoms C-2 and C-3. Further, such additional carbon atoms are denoted as C-2a and C-2b, counting from the C-2 to the C-3 carbon atoms, respectively.

The novel prostacyclin analogs herein wherein R$_8$ is hydrogen or hydroxymethyl are respectively referred to as 11-deoxy-PGI$_1$-type or 11-deoxy-11-hydroxymethyl-PGI$_1$-type compounds. Additionally, when Y$_1$ is cis—CH=CH—, —CH$_2$CH$_2$—, or —C≡C—, the novel compounds thereby referred to are named as 13-cis-PGI$_1$-type, 13,14-dihydro-PGI$_1$-type, or 13,14-didehydro-PGI$_1$-type compounds.

Novel compounds herein wherein M$_1$ is

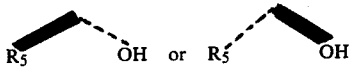

and R$_5$ is methyl are referred to as 15-methyl-PGI$_1$-type compounds.

With the exception of the 13-cis-PGI$_1$-type compounds described above, all the above compounds exhibiting a hydroxy in the beta configuration at C-15 are additionally referred to as 15-epi-PGI$_1$-type compounds. For the 13-cis-PGI$_1$-type compounds herein, only compounds exhibiting the hydroxy in the alpha configuration at C-15 are referred to as 15-epi-PGI$_1$-type compounds. The rationale for this system of nomenclature with respect to the natural and epimeric configurations at C-15 is described in U.S. Pat. No. 4,016,184, issued Apr. 5, 1977.

When R$_7$ is —(CH$_2$)$_m$—CH$_3$, wherein m is as defined above, the novel compounds herein are named as 19,20-dinor-PGI$_1$-type, 20-nor-PGI$_1$-type, 20-methyl-PGI$_1$-type or 20-ethyl-PGI$_1$-type compounds when m is one, 2, 4, or 5, respectively;

When R$_7$ is

wherein T and s are as defined above, and neither R$_3$ nor R$_4$ is methyl, the novel compounds herein are named as 16-phenyl-17,18,19,20-tetranor-PGI$_1$-type compounds, when s is zero. When s is one, 2, or 3, the corresponding compounds are named as 16-(substituted phenyl)-17,18,19,20-tetranor-PGI$_1$-type compounds. When one and only one of R$_3$ and R$_4$ is methyl or both R$_3$ and R$_4$ are methyl, then the corresponding compounds wherein R$_7$ is as defined in this paragraph are named as 16-phenyl- or 16-(substituted phenyl)-18,19,20-trinor-PGI$_1$-type; or 16-methyl-16-phenyl- or 16-methyl- or 16-(substituted phenyl)-18,19,20-trinor-PGI$_1$-type compounds, respectively.

When R$_7$ is

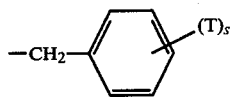

wherein T and s are as defined above, the novel compounds herein are named as 17-phenyl-18,19,20-trinor-PGI$_1$-type compounds, when s is zero. When s is one, 2, or 3, the corresponding compounds are named as 17-(substituted phenyl)-18,19,20-trinor-PGI$_1$-type compounds.

When R$_7$ is

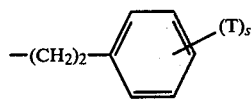

wherein T and s are as defined above, the novel compounds herein are named as 18-phenyl-19,20-dinor-PGI$_1$-type compounds, when s is zero. When s is one, 2, or 3, the corresponding compounds are named as 18-(substituted phenyl)-19,20-dinor-PGI$_1$-type compounds.

When R$_7$ is

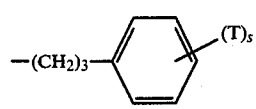

wherein T and s are as defined above, the novel compounds herein are named as 19-phenyl-20-nor-PGI$_1$-type compounds, when s is zero. When s is one, 2, or 3, the corresponding compounds are named as 19-(substituted phenyl)-20-nor-PGI$_1$-type compounds.

When R$_7$ is

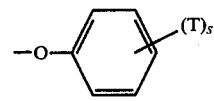

wherein T and s are as defined above, and neither R$_3$ nor R$_4$ is methyl, the novel compounds herein are named as 16-phenoxy-17,18,19,20-tetranor-PGI$_1$-type compounds, when s is zero. When s is one, 2, or 3, the corresponding compounds are named as 16-(substituted phenoxy)-17,18,19,20-tetranor-PGI$_1$-type compounds. When one and only one of R$_3$ and R$_4$ is methyl or both R$_3$ and R$_4$ are methyl, then the corresponding compounds wherein R$_7$ is as defined in this paragraph are named as 16-phenoxy- or 16-(substituted phenoxy)-18,19,20-trinor-PGI$_1$-type compounds or 16-methyl-16-phenoxy- or 16-(substituted phenoxy)-18,19,20-trinor-PGI$_1$-type compounds, respectively.

When at least one of R$_3$ and R$_4$ is not hydrogen, then (except for the 16-phenoxy or 16-phenyl compounds discussed above), there are thusly described the 16-methyl-PGI$_1$-type (one and only one of R$_3$ and R$_4$ is methyl), 16,16-dimethyl-PGI$_1$-type (R$_3$ and R$_4$ are both methyl), 16-fluoro-PGI$_1$-type (one and only one of R$_3$ and R$_4$ is fluoro), and 16,16-difluoro-PGI$_1$-type (R$_3$ and R$_4$ are both fluoro) compounds. For those compounds wherein R$_3$ and R$_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

The novel prostacyclin intermediates herein are further named as 2-decarboxy-2-hydroxymethyl-PGI$_1$-type compounds.

When X$_1$ is —COL$_4$, the novel compounds herein are named as PGI$_1$-type, amides. Further, when X$_1$ is —COOR$_1$, the novel compounds herein are named as PGI$_1$-type, esters and PGI$_1$-type, salts when R$_1$ is not hydrogen.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

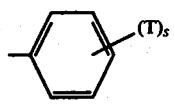

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,3,5-trimethylphenyl, (o-, m, p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-methoxyphenyl, (o-, m-, or p-)ethoxyphenyl, (4- or 5-)chloro-2-methoxyphenyl, and 2,4-dichloro(5- or 6-)methylphenyl.

Examples of phenyl esters substituted in the para position (i.e., $X_1$ is —COOR$_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzoylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel prostacyclin amides herein (i.e., $X_1$ is —COL$_4$) include the following:

(1) Amides within the scope of alkylamino groups of the formula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopehtylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-methyl-N-cyclohexylamide, dicyclopentylamide, and dicyclohexylamide. Amides within the scope of aralkylamino are benzylamide, 2-phenylethylamide, 2-phenylethylamide, N-methyl-N-benzylamide, and dibenzylamide. Amides within the scope of substituted phenylamino are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamino are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylethylamide, 4-methyl-β-pyridylethylamide, 4-chloro-α-pyridylethylamide, 4-chloro-β-pyridylethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, and 4-chloro-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxyethyl)propylamide, and α,α-dimethyl-β-hydroxyethylamide. Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)1-hdroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula $-NR_{23}COR_{21}$ are methylcarbonylamide, ethylcarbonylamide, phenylcarbonylamide, and benzylcarbonylamide, Amides within the scope of sulfonylamino of the formula $-NR_{23}SO_2R_{21}$ are methylsulfonylamide, ethylsulfonylamide, phenylsulfonylamide, p-tolylsulfonylamide, benzylsulfonylamide.

(4) Hydrazides within the scope of the above hydrazino groups are hydrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine.

The term "pharmacologically acceptable cation" refers to those pharmacologically acceptable salts of the prostacyclin-type carboxylic acids which are conventionally employed with prostaglandins. In particular, such pharmacologically acceptable salts include pharmacologically acceptable metal cations, amine cations, and quarternary ammonium cations. Additionally basic amino acids such as arginine and lysine are employed. Further, certain amine cations such as THAM [tris(hydroxymethyl)amino methyl] and adamantanamine are especially useful for the present purposes. Additionally, U.S. Pat. No. 4,016,184, issued Apr. 5, 1977 (particularly column 29), describes salts which are likewise preferred for the present purposes.

The novel prostacyclin analogs disclosed herein are all inhibitors of endoperoxide cyclooxygenase, an enzyme which converts unsaturated fatty acids (e.g., arachadonic acid) to prostaglandin endoperoxide intermediate (e.g., $PGH_2$). The inhibition of this enzyme (also known as PG synthetase) is established as a standard in vitro laboratory test which measures oxygen uptake in the conversion of the unsaturated fatty acid to the endoperoxides, e.g.,

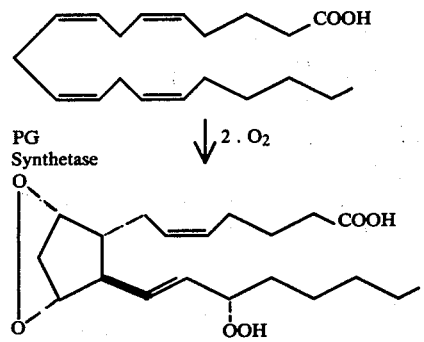

Hence the inhibition of oxygen uptake is a measure of the inhibition of the enzyme itself. The efficacy of the novel prostacyclin analogs herein as inhibitors of cyclooxygenase (PG synthetase) is indicated in the following comparison between 2-(acetylozy)benzoic acid (aspirin) and 7,8-didehydro-6β-PGI₁, methyl ester:

| Compound | Concentration | Percent inhibition of Oxygen Uptake |
|---|---|---|
| 2-(Acetyloxy)-benzoic acid | 5 × 10⁻⁵M | Inactive |
| 7,8-Didehydro-6β-PGI methyl ester | 5 × 10⁻⁴M | 46% |
| 2-(Acetyloxy)-benzoic acid | 5 × 10⁻⁴M | 100% |

For further description of PG synthetase inhibition, see Vane, Nature New Biology, 231–232 (1971) and Takeguchi, et al., Prostaglandins 2:169 (1972).

Because of this biological activity, the novel prostacyclin analogs herein are useful for antiinflammatory purposes, and are used for this purpose in the same manner and with similar dosages as 2-(acetyloxy)benzoic acid.

For example, these novel prostacyclin analogs are useful as antiinflammatory agents in mammals and especially humans, and for this purpose, are administered systemically and preferably orally. For oral administration, a dose range of 0.01 to 100 µg. per kg. of human body weight is used to give relief from pain associated with inflammatory disorders such as rheumatoid arthritis. They are also administered intravenously in aggravated cases of inflammation, preferably in a dose range 0.01 to 100 µg. per kg. per minute until relief from pain is attained. When used for these purposes, these novel prostacyclin analogs cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

Within the scope of the novel prostacyclin analogs described above, certain compounds are preferred in that they exhibit increased potency, selectivity of action, or otherwise represent especially convenient and useful agents, especially for the preferred uses described above.

Accordingly, preferred compounds are those wherein g is the integer one or 3, most preferably being one. With respect to the $Y_1$ moiety, preferred compounds are those wherein $Y_1$ is trans—CH=CH—, —CH$_2$CH$_2$— or —C≡C—, the most especially preferred compounds being those wherein $Y_1$ is trans—CH=CH—.

With respect to the $L_1$ moiety, those compounds wherein $R_3$ and $R_4$ are the same are preferred. Further preferred are those compounds herein wherein at least $R_3$, $R_4$, and $R_5$ is hydrogen. In the event $Y_1$ is cis—CH=CH— or —C≡C—, compounds wherein $R_3$, $R_4$, and $R_5$ are all hydrogen are preferred.

With respect to the integers m, h, and s, it is preferred that m be the integer 3, h be the integer zero or one and s be the integer zero or one. Further, T is preferably chloro, fluoro, or trifluoromethyl.

Further preferred are the carboxylic acids or esters, especially the p-substituted phenyl esters. With respect to the novel amides herein, preferred compounds are those wherein $R_{21}$ and $R_{22}$ are preferably hydrogen or alkyl of one to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further, $R_{23}$ is preferably hydrogen.

The charts herein describe the method by which the novel prostacylcin analogs herein are prepared from known or readily synthesized starting materials.

With respect to Charts A-C; g, $L_1$, $M_1$, $R_7$, $R_8$, and $X_1$ are as defined above.

CHART A

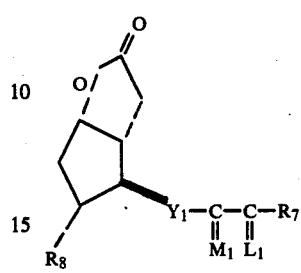 XXI

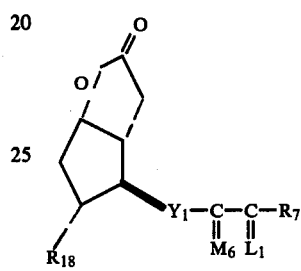 XXII

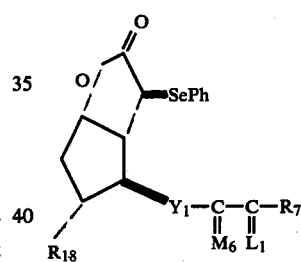 XXIII

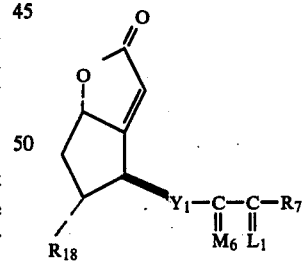 XXIV

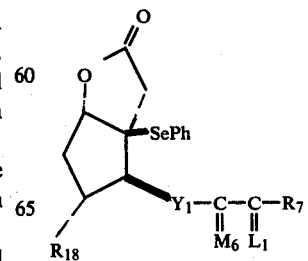 XXV

CHART A
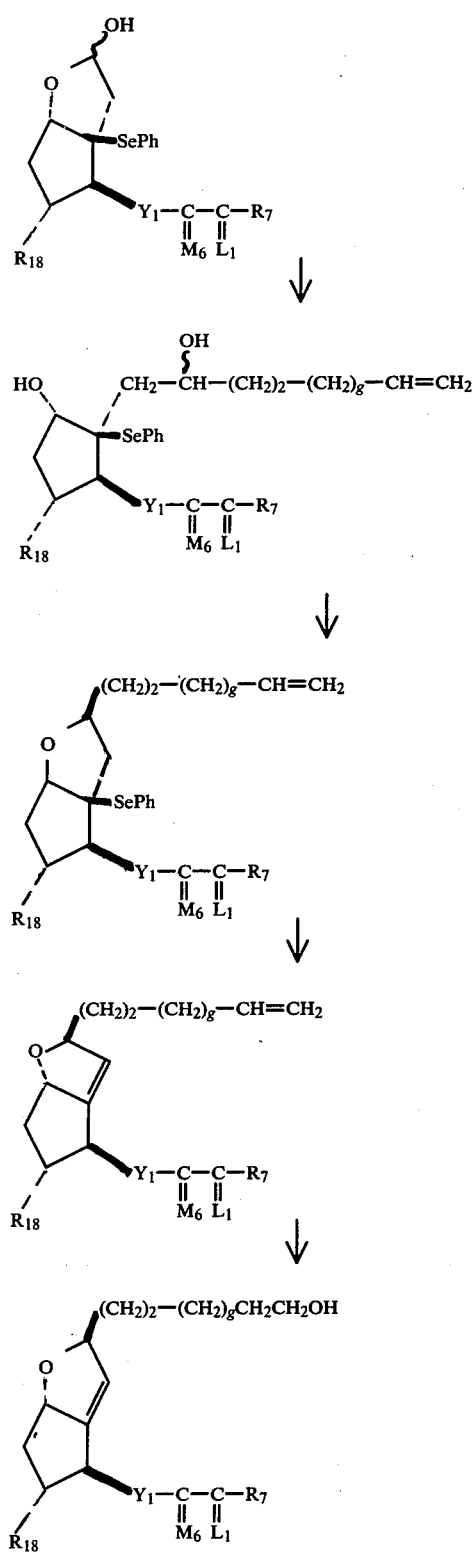
CHART B
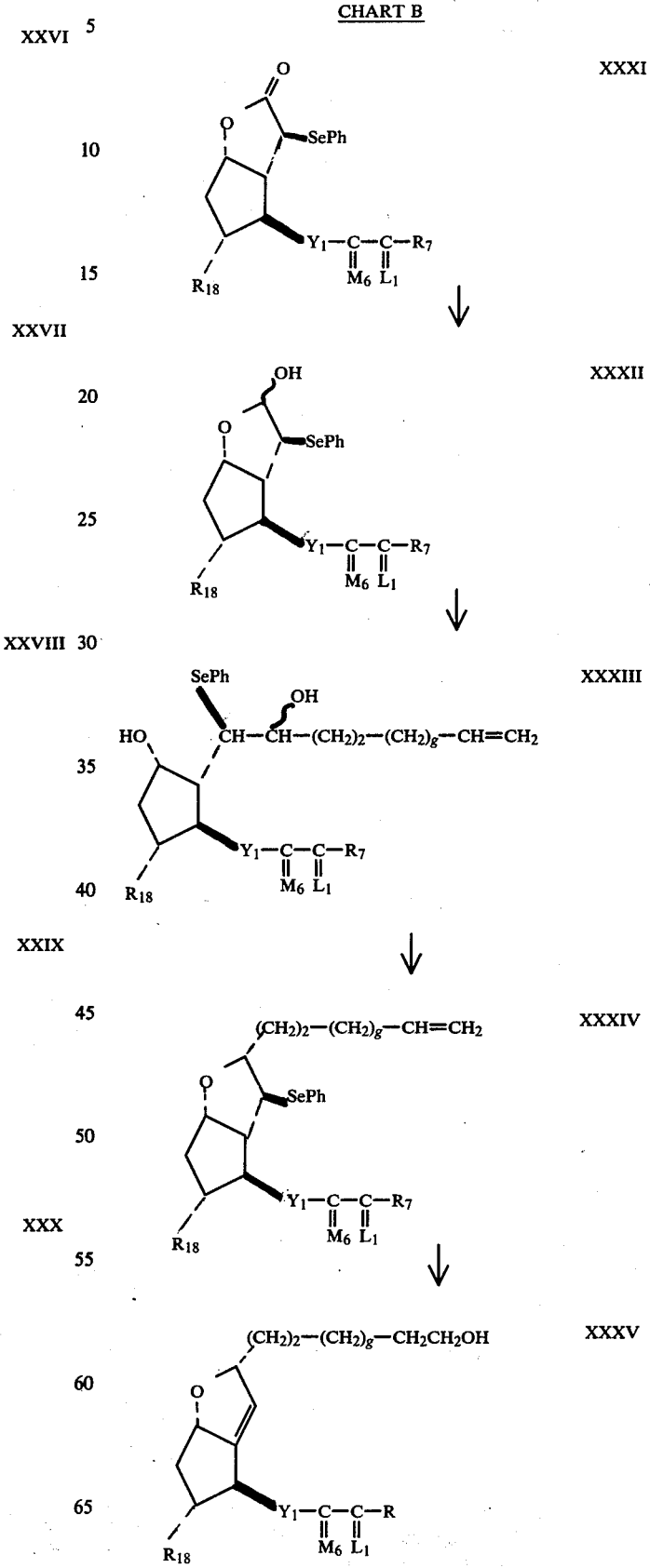

CHART C

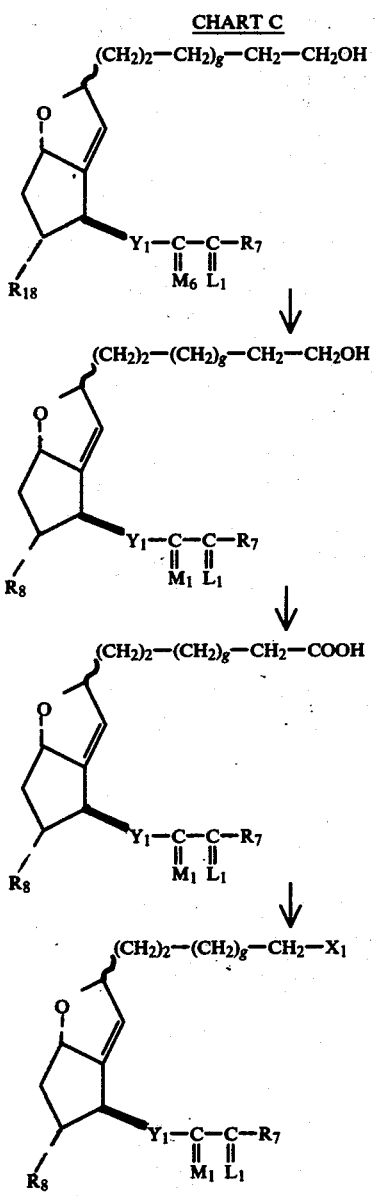

—SePh is phenylselenidyl. $R_{18}$ and $M_6$ are respectively the hydroxyl-derivatized forms of $R_8$ and $M_1$. Appropriate hydroxyl derivatives include acid hydrolyzable stable silyl groups (e.g., t-butyldimethylsilyl) and acetaltype blocking groups (e.g., tetrahydropyranyl). Examples of the appropriate derivatives and the methods for their introduction and subsequent hydrolysis are described in U.S. Pat. No. 4,016,184.

With respect to Chart A, the formula XXI compound is known in the art or prepared by methods readily available in the art.

Formula XXII compound is then prepared from the formula XXI compound by hydroxyl-derivatization. In this manner, the hydroxyl group in the $M_1$ moiety and the hydroxy group, if any, of the $R_8$ moiety are transformed to corresponding silyl or acetal ethers. As indicated above, methods for the derivatization are known in the art. See U.S. Pat. No. 4,016,184.

The formula XXIII compound is then prepared from the formula XXII compound by phenylselenidylation. Phenylselenidylation is accomplished by methods known in the art. For example, the formula XXII lactone, placed in a solution of n-butyllithium in hexane and diisopropylamine in tetrahydrofuran, is reacted with phenylselenyl chloride to yield the desired product. This phenylselenidyl lactone (formula XXIII) is then transformed to the corresponding alpha-beta unsaturated lactone of formula XXIV by reaction with hydrogen peroxide. For this purpose the phenylselenidyl lactone is dissolved in an organic solvent at room temperature and aqueous hydrogen peroxide is added dropwise. The reaction then proceeds on vigorous stirring of the mixture, yielding the desired product by solvent evaporation.

The formula XXV is then prepared from the formula XXIV compound by a second phenylselenidylation. This reaction proceeds by combining diphenyl diselenide to a solution of a borohydride reducing agent (e.g., sodium borohydride) in an alcoholic (e.g., ethanol) solvent. When the preparation of the reagent is complete (i.e., evolution of hydrogen gas has ceased), the formula XXIV product is then combined with the phenylselenidyl anion reagent and the reaction allowed to proceed to completion. When thin layer TLC indicates the reaction to be complete, the desired formula XXV product is then isolated by conventional techniques.

The formula XXVI compound is then prepared from the formula XXV compound by reduction of the lactone of formula XXVI to the corresponding lactol. For this purpose, diisobutylaluminum hydride is employed, at low temperature. Accordingly, the reaction proceeds at about $-78°$ C. and is ordinarily complete within several minutes. Thereafter the pure formula XXVI compound is recovered by conventional techniques. For example, the reaction mixture is filtered to remove the aluminum salts and thereafter concentrated to the desired product.

The formula XXVII compound is then prepared from the formula XXVI compound by a Grignard reaction. For this purpose, a Grignard reagent is prepared from the appropriate ω-bromo-1-alkene (i.e., pentene, hexene, or heptene) by stirring a suspension of the halide compound and magnesium turnings in diethyl ether. After preparation of the Grignard reagent, it is cooled (e.g., to about $0°-5°$ C.) and added dropwise to a solution containing the formula XXVI compound. When the reaction is complete, the formula XXVII compound is then extracted into an organic solvent and concentrated to yield the desired product.

The formula XXVIII compound is then prepared from the formula XXVII compound by reaction with an aryl or alkyl sulfonyl halide (e.g., p-toluenesulfonyl chloride or methylsufonyl chloride). For example, the formula XXVII compound is reacted with the sulfonyl halide in an amine base at about ambient temperature for several days when p-toluenesulfonyl chloride or for several minutes at $-78°$ C. when methanesulfonyl chloride is employed. In either event when silica gel TLC analysis indicates the formula XXVII starting material is complete consumed, the formula XXVIII product is recovered from the product mixture by chromatography and conventional isolation techniques. In particular, the formula XXVIII product is separated from 2-decarboxy-2-methylene-9-deoxy-8,9-didehydro-PG-type contaminants.

The formula XXIX compound is then prepared from the formula XXVIII compound by dehydrophenylselenidylation, in the manner described for the preparation of the formula XXIV compound from the formula XXIII compound. Thereafter, the formula XXX prostacyclin intermediate is prepared from the formula XXIX compound by transformation of the terminal olefin to a primary alcohol. This transformation proceeds by any one of a number of methods known in the art for effecting such transformations. For example, 9-borobicyclo-[3.3.1]nonane is added to the formula XXIX terminal olefin in an organic solvent (e.g., tetrahydrofuran). After stirring for several hours at about 0° C., the reaction is quenched by addition of strong mineral base, e.g., sodium hydroxide, and hydrogen peroxide. Pure title formula XXX product is then recovered by conventional means.

Alternatively to the procedure described in Chart A, the formula XXX compound is prepared from the formula XXVIII compound by first oxidizing the terminal olefin to the corresponding primary alcohol and thereafter dehydrophenylselenidylating the primary alcohol thusly prepared.

Chart B provides a method whereby the formula XXXI compound (the formula XXIII compound of Chart A) is transformed to the formula XXXV 6α-PGI$_1$-type intermediate corresponding 6β-PGI$_1$-type intermediate of formula XXX of Chart A.

With respect to Chart B, the formula XXXI transformed to the formula XXXII compound by reducing the formula XXXI lactone to the corresponding lactol. This transformation is accomplished by the method described in Chart A for the transformation of the formula XXV to the formula XXVI compound.

Thereafter, the formula XXXIII is prepared from the formula XXXII compound by a Grignard reaction, following the procedure described in Chart A for the transformation of the formula XXVI compound to the formula XXVII compound.

Thereafter, the formula XXXIII compound is cyclized to the corresponding XXXIV compound by procedures similar to those described in Chart A for the cyclization of the formula XXVII compound of the formula XXVIII compound. In particular, the formula XXXIII compound is reacted with an aryl or alkyl sulfonyl chloride in an amine base (e.g., triethylamine) and a suitable organic solvent (e.g., dichloromethane). The reaction thereafter proceeds in the manner described in Chart A for the recovery and isolation of the formula XXXIV cyclic product. This formula XXXIV product is then transformed to the formula XXXV compound by the methods of Chart A for the transformation of the formula XXVIII compound to the formula XXX compound.

Finally, Chart C provides a method whereby the formula XLI compound is transformed to the novel formula XLIII and formula XLIV prostacyclin analogs of the present invention. The formula XLI compound represents either the 6α-PGI$_1$-type compound of Chart B (formula XXXV) or the 6β-PGI$_1$-type compound of Chart A (formula XXX).

The formula XLII compound is prepared from the formula XLI compound by hydrolysis of the silyl or acetaltype blocking groups of the formula XLI compound. This transformation proceeds by methods known in the art, namely, under mild acidic conditions. For example, mixtures of water, acedic acid and tetrahydrofuran are employed in the hydrolysis of acetal-type blocking groups while dilute mineral acid is effective in hydrolyzing the silyl groups.

The formula XLII primary alcohol is then oxidyzed to the corresponding carboxylic acid of formula XLIII employing an Adams catalyst. See Fieser and Fieser, Reagents for Organic Synthesis, Vol. 1, page 890, John Wiley & Sons, New York, New York (1967).

Thereafter, this carboxylic acid is transformed to the corresponding PGI$_1$-type salt, ester, or amide by methods known in the art for preparing these respective derivatives of PG-type carboxylic acids.

The pharmacologically acceptable salts of these carboxylic acids are obtained by neutralization with a corresponding base. Conventional techniques of isolation and recovery of the salt are employed.

With respect to the novel PG-type amides (X$_1$ is —COL$_4$) and esters, especially p-substituted phenyl esters (R$_1$ is p-substituted phenyl, such compounds are prepared as follows:

With regard to the preparation of the esters, especially p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PGI-type carboxylic acids, the corresponding carboxyamides are then prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741, describing the preparation of carbonylamido and sulfonylamido derivatives of prostaglandin-type free acids.

The preferred method by which the present amido and cycloamido derivatives of the novel prostacyclin-type free acids are prepared is, first by transformation of such free acids to corresonding mixed acid anhydrides. By this procedure, the prostaglandin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGI-type free acid is mixed with both the tertiary amine base and the chloroformate in a suitable solvent (e.g., aqueous tetrahydrofuran), allowing the reaction to proceed at −10° to 20° C.

Thereafter, the mixed anhydride is converted to the corresponding amids or cycloamido derivative by reaction with the amine corresponding to the amide to be prepared. In the case where the simple amide (—NH$_2$) is to be prepared, the transformation proceeds by the addition of ammonia. Accordingly, the corresponding amide (or ammonia) is mixed with the mixed anhydride at or about −10° to +10° C., until the reaction is shown to be complete. For highly volatile amides, acid addition salts thereof (e.g., methylamine hydrochloride) are employed in place of the corresponding free base (e.g., methylamine).

Thereafter, the novel PGI-type amido or cycloamido derivative is recovered from the reaction mixture by conventional techniques.

The carbonylamido and sulfonylamido derivatives of the presently disclosed PGI-type compounds are likewise prepared by known methods. See, for example, U.S. Pat. No. 3,954,741 for description of the methods by which such derivatives are prepared. By this known method, the prostacyclin-type free acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PGI-type mixed anhydride, employing the method described above for the preparation of the amido and cycloamido derivatives. Thereafter, the sodium salt of the corresponding sulfonamide is reacted with the mixed anhydride and hexamethylphosphoramide. The pure PGI-type sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method, methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

With regard to the phenacyl or substituted phenacyl esters herein, see U.S. Pat. No. 3,979,440 for a description of their preparation.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer or an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M Hamberg and B. Samuelsson, J. Biol. Chem. 241, 257 (1955).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-John or Thomas-Hoover melting point apparatus.

THF refers to tetrahydrofuran.

Specific Rotations, ($\alpha$), are determined for solutions of a compound in the specified solvent at ambient temperature with a Perkin-Elmer Model 141 Automatic Polarimeter.

EXAMPLE 1

2-Decarboxy-2-hydroxymethyl-7,8-didehydro-6$\beta$-PGI$_1$ (Formula XLII): g is one, R$_8$ is hydroxy, Y$_1$ is trans-CH=CH—, R$_3$ and R$_4$ of the L$_1$ moiety and R$_5$ of the M$_1$ moiety are all hydrogen, and R$_7$ is n-butyl). Refer to Chart A.

A. To a magnetically stirred solution of 3$\alpha$,5$\alpha$-dihydroxy-2$\beta$-(3$\alpha$-hydroxy-trans-1-octenyl)-1$\alpha$-cyclopentane acetic acid,$\gamma$-lactone (8.95 g) in 85 ml of dimethylformamide is added 4.77 g of imidazole and 10.63 g of dimethyl-t-butylsilyl chloride. After addition, the reaction mixture is cooled to 0° C. for 10 min and thereafter allowed to warm to ambient temperature. After about 16 hrs, the resulting mixture is poured into 800 ml of ice water and the aqueous solution is extracted with 900 ml of diethyl ether. The ethereal extracts are then washed with water (100 ml) dried over anhydrous sodium sulfate, and concentrated under reduced pressure to yield 15.23 g of the formula XXII compound: 3$\alpha$,5$\alpha$-dihydroxy-2$\beta$-(3$\alpha$-hydroxy-trans-1-octenyl)-1$\alpha$-cyclopentaneacetic acid,$\gamma$-lactone, bis(t-butyldimethylsilyl ether) as a waxy white solid. Melting range is 83°–86° C. Silica gel TLC Rf is 0.64 in ethyl acetate in Skellysolve B (1:3). NMR absorptions are observed at 5.63-5.33, 5.07-4.68, 4.26-3.78, 3.10-1.85, 1.84-1.10, 0.88, and 0.01 $\delta$. Infrared absorptions are observed at 2950, 1760, 1450, 1440, 1370, 1340, 1250, 1160, 1120, 1085, 998, 970, 935, 895, 835, and 775 cm$^{-1}$.

B. n-Butyllithium (1.6 M in hexane) is added under a nitrogen atmosphere to a magnetically stirred solution of diisopropylamine (2.2 g) and 75 ml of tetrahydrofuran at −78° C. After stirring for 8 min at −78° C., the reaction product of Part A is added dropwise over a period of about 4 min. When the addition is complete, phenylselenyl chloride (4.02 g) and 2 ml of tetrahydrofuran is added over 2 min. The reaction mixture is then stirred for 20 min. at −78° C. and the resulting solution poured into 150 ml of saturated aqueous ammonium chloride in crushed ice. The aqueous solution is then extracted with diethyl ether (700 ml) and the combined ethereal extracts washed with water, brine, and dried over anhydrous sodium sulphate. Concentration under reduced pressure yields 14.41 g of a viscous oil, containing a 1:1 ratio of the formula XXII reactant and formula XXIII product; 3$\alpha$,5$\alpha$-dihydroxy-2$\beta$-(3$\alpha$-hydroxy-trans-1-octenyl)-1$\alpha$-cyclopentanephenylselenidylacetic acid, $\gamma$-lactone, bis(t-butyleimthylsilyl ether).

Chromatographing on silica gel (a Skellysolve B and ethyl acetate eluent mixture, 25:1) yields pure formula XXIII product as a viscous orange oil. Silica gel TLC Rf is 0.54 in Skellysolve B and ethyl acetate (9:1). NMR absorptions are observed at 7.88-7.48, 7.44-7.14, 5.54-5.28, 4.58-4.19, 4.17-3.77, 3.75-3.57, 2.78-1.77, 1.75-1.10, 0.89, and 0.85δ. Infrared absorptions are observed at 2850, 1750, 1560, 1450, 1420, 1345, 1240, 1160, 1115, 1080, 1000, 965, 935, 900, 835, 775, 735, and 683 cm$^{-1}$.

C. To a vigorously stirred solution of the reaction product of Part B (5.00 g) and 180 ml of methylene chloride at ambient temperature is added dropwise over a period of 20 min an aqueous solution of hydrogen peroxide (prepared from 8.7 g of 30% hydrogen peroxide diluted with 16 ml of water). Vigorous stirring is continued for 2 hr at ambient temperature whereupon the aqueous layer is separated and the methylene chloride solution successively washed with ice water, sodium bicarbonate, and brine. Drying over sodium sulfate and concentrating under reduced pressure yields 4.67 g of crude formula XXIV product as a viscous oil. Chromatography on 200 g of silica gel packed and eluted with Skellysolve B in ethyl acetate (15:1) yields 2.86 g of pure 3α,5α-dihydroxy-2β-(3α-hydroxy-trans-1-octenyl)-1α-cyclopentane-(α,β-didehydro)acetic acid, γlactone, bis(t-butyldimethylsill ether) as a waxy solid. Melting range is 36.5°-38° C. Silica gel TLC Rf is 0.22 in Skellysolve B and ethyl acetate (15:1). NMR absorptions are observed at 5.82-5.47, 5.13-4.67, 4.48-3.89, 3.37-3.07, 2.88-2.37, 2.18-1.05, 0.85, and 0.04δ. Infrared absorptions are observed at 2960, 1760, 1640, 1450, 1435, 1245, 1215, 1145, 1085, 1000, 965, 930, 890, 835, and 775 cm$^{-1}$. The high resolution mass spectrum exhibits a peak at 494.3245, while other mass spectral peaks are observed at 479, 437, 423, 362, 336, 279, and 215.

D. Diphenyl diselenide (4.78 g) is added in several portions to a magnetically stirred solution of sodium borohydride (1.26 g) in 16 ml of absolute ethanol cooled in an ice water bath. After evolution of hydrogen ceases, the reaction product of Part C (6.86 g) in 50 ml of absolute ethanol is added. The ice water bath is then removed and stirring continued for 1.5 hr at ambient temperature. Thereafter the resulting mixture is poured in 500 ml of saturated brine and extracted with diethyl ether. The ethereal extracts are then washed with ice water and the aqueous washings are back-extracted with diethyl ether and the combined ethereal extracts dried over sodium sulfate. Concentration under reduced pressure yields 10 g of a crude yellow oil, 3α,5α-dihydroxy-2β-(3α-hydroxy-trans-1-octenyl)-1β-phenylselenidyl-1α-cyclopentaneacetic acid γ-lactone, bis(t-butyldimethylsilyl ether). Chromatography on 600 g of silica gel packed and eluted with Skellysolve B in ethyl acetate (20:1) yields 5 g of pure product of the colorless oil. Silica gel TLC Rf is 0.60 in ethyl acetate and benzene (1:50). NMR absorptions are observed at 5.75-5.22, 5.68-5.45, 4.84-4.58, 4.43-3.93, 2.79-2.13, 2.05-1.83, 1.78-1.06, 0.89, 0.83, 0.03, and 0.0δ. Infrared absorptions are observed at 2950, 1785, 1575, 1460, 1430, 1350, 1250, 1170, 1120, 1090, 1000, 965, 890, 835, 765, 740, and 695 cm$^{-1}$. The mass spectrum exhibits a weak molecular ion at 652, a high resolution peak at 595.2165 and other peaks at 581, 521, 463, 437, 337, and 215.

E. Diisobutylaluminum hydride (5.11 ml of a 1.5 M solution in toluene) is added dropwise over 4 min to a magnetically stirred solution of the reaction product of Part D (5.00 g) in 70 ml of toluene cooled to −78° C. After stirring for 20 min at −78° C., 4 ml of saturated aqueous sodium sulfate is added and the reaction mixture allowed to warm to ambient temperature. The reaction mixture is then diluted with 400 ml of diethyl ether and 4 g of powdered sodium sulfate is added. Stirring is then continued for 30 min at ambient temperature, causing the coagulation of the aluminum salts. Suction filtration through diatomaceous earth and concentration of the filtrate under reduced pressure yields 4.78 g of pure 3α,5α-dihydroxy-2β-(3α-hydroxy-trans-1-octenyl)-1β-phenylseledinyl-1α-cyclopentaneacetic acid, γ-lactol, bis(t-butyldimethylsilyl ether). Silica gel TLC Rf is 0.26 in ethyl acetate and Skellysolve B (1:6). NMR absorptions are observed at 7.82-7.43, 7.43-7.16, 5.79-5.53, 5.53-4.99, 4.52-3.53, 3.27-2.84, 2.72-1.14, 0.92, 0.88, 0.85, 0.09, 0.03, and 0.0δ. Infrared absorptions are observed at 3420, 2950, 1575, 1460, 1430, 1350, 1250, 1110, 1020, 1000, 965, 935, 835, 775, 740, and 690 cm$^{-1}$. The mass spectrum exhibits a debutylated molecular ion as a high resolution peak at 669.2704, a weak molecular ion at 726, and other peaks at 511 and 215.

F. To a magnetically stirred suspension of 0.877 g of magnesium turnings in 50 ml of anhydrous diethyl ether is added under a nitrogen atmosphere at ambient temperature 5.22 g of 5-bromo-1-pentene. Stirring is then maintained at ambient temperature for 45 min, at which time the formation of the Grignard reagent is complete. Thereafter the Grignard reagent is cooled to 0° C. and added dropwise over 3 min to a solution of the reaction product of Part E in 100 ml of diethyl ether at 0°-5° C. The resulting mixture is then stirred for an additional 1.5 hr at 0°-5° C. whereupon the reaction mixture is poured into 200 ml of ice water containing 100 ml of saturated aqueous ammonium chloride. The aqueous mixture is then extracted with diethyl ether and the ethereal extracts washed with 150 ml. of brine, dried over sodium sulphate and concentrated under reduced pressure to yield 5.46 g of a crude formula XXVII yellow oil: 2-decarboxy-2-methylene-6-hydroxy-8β-phenylselenidyl-PGF$_{1α}$, 11,15-bis(t-butyldimethylsilyl ether). Chromatography of this crude product on 415 g of silica gel packed and eluted with Skellysolve B in ethyl acetate (9:1) yields 0.82 g of essentially pure product and 4.22 g of pure product as a colorless oil. Silica gel TLC Rf is 0.21 in ethyl acetate and benzene (1:20). NMR absorptions are observed at 7.82-7.52, 7.41-7.14, 6.14-5.41, 5.18-4.75, 4.63-3.45, 2.75-1.14, 0.94, 0.87, 0.08, and 0.0 δ. Infrared absorptions are observed at 3260, 2850, 1760, 1660, 1570, 1450, 1345, 1245, 1090, 990, 965, 905, 865, 835, 775, 735, and 690 cm$^{-1}$.

G. (Procedure A) p-Toluenesulfonyl chloride (5.27 g) is added at ambient temperature in one portion to the reaction product of Part F dissolved in 33 ml of pyridine. The resulting solution is then magnetically stirred for 4 days in an oil bath maintained at 35°-40° C. Thereupon 15 ml of water is added and the stirring continued for 1.5 hr at ambient temperature. The reaction mixture is then poured into 300 ml of ice water and the aqueous solution extracted with 600 ml of diethyl ether. The ethereal extracts are then successively washed with 100 ml of saturated aqueous sodium bicarbonate, 75 ml of 5% aqueous sodium bicarbonate, and brine. The organic washings are then back-extracted with diethyl ether (200 ml), and the combined organic extracts dried over magnesium sulfate and concentrated under reduced pressure to yield 4.20 g of crude formula XXVIII 2-decarboxy-2-methylene-8β-phenylselenedyl-PGI$_1$, 11,15-bis(t-butyldimethyl-silyl ether). Chromtography of the crude product on 400 g of silica gel packed and eluted with Skellysolve B in ethyl acetate (75:1) yields a mixture of formula XXVIII product and an impurity. Thereafter high pressure liquid chromatography with the same solvent system yields 0.8 g of pure product.

G. (Procedure B) To a magnetically stirred solution of the reaction product of Part F (0.724 g) and triethylamine (5.05 g) in 23 ml of methylene chloride cooled to −78° C. is added slowly methanesulfonyl chloride (0.228 g). A TLC analysis taken immediately after the methanesulfonyl chloride addition indicates the reaction is complete and the mixture is then diluted with methylene chloride. This organic solution is then washed with water and saturated brine, dried over sodium sulfate, and concentrated under reduced pressure to yield 7.50 g of crude formula XXVIII product. This product is then chromatographed in 125 g of silica gel packed and eluted with Skellysolve B and ethyl acetate, yielding 0.3 g of pure formula XXVIII product.

The formula XXVIII product as obtained by either procedure exhibits the following physical/analytical characteristics:

Silica gel TLC Rf is 0.67 in ethyl acetate and Skellysolve B (1:15). NMR absorptions are observed at 7.73-7.42, 7.42-7.04, 5.95-5.31, 5.08, 4.63, 4.38-3.68, 2.67-1.10, 0.92, 0.86, 0.08, and 0.0$\delta$. Infrared absorptions are observed at 2950, 1635, 1570, 1460, 1430, 1250, 1090, 1000, 965, 935, 910, 835, 775, 740, and 690 cm$^{-1}$. The mass spectrum exhibits a weak molecular ion at 706, a debutylated high resolution peak at 649.3055, and other peaks at 548, 517, 391, 260, 215, and 158.

H. Following the procedure described in Part C above, treatment of the reaction product of Part G (0.64 g) in 15 ml of methylene chloride with 10% aqueous hydrogen peroxide (3.08 g) yields 0.551 g of formula XXIX compound: 2-decarboxy-2-methylene-7,8-didehydro-6$\beta$-PGI$_1$, 11,15-(t-butyldimethyldilyl ether). Chromatography on 125 g of silica gel, packed and eluted with Skellysolve B in ethyl acetate (50:1) yields 2.66 g of pure formula XXIX product.

Silica gel TLC Rf is 0.63 in ethyl acetate and benzene (1:50). NMR absorptions are observed at 6.12-5.32, 5.27-4.51, 4.28-3.83, 3.08-2.78, 2.55-1.07, 0.87, and 0.2-0.01$\delta$. Infrared absorptions are observed at 2950, 1640, 1460, 1350, 1250, 1220, 1080, 1005, 970, 935, 910, 835, and 775 cm$^{-1}$. The mass spectrum exhibits a high resolution peak at 548.4059 and other peaks at 553, 491, 479, 477, 401, 390, 333, 321, 219, and 215.

I. 9-Borobicyclo-[3.3.1]nonane(9-BBN, 2.63 ml of a 0.5 M solution in tetrahydrofuran) is added dropwise over 5 min to a solution of the reaction product of Part H (0.266 g) in 16 ml of tetrahydrofuran at 0° C. After stirring for 2.5 hr. at 0° C., 1 ml of water is added followed by addition of 3 N aqueous sodium hydroxide (0.5 ml) and 30% aqueous hydrogen peroxide (0.30 ml). The resulting mixture is then stirred at ambient temperature to 20 min; diluted by addition of 150 ml of diethyl ether; and the ethereal solution successively washed with 50 ml of brine, water, and brine. The aqueous washings are then back-extracted with diethyl ether and the ethereal extracts dried over sodium sulfate and concentrated under reduced pressure to yield 3.97 g of crude formula XXX 2-decarboxy-2-hydroxymethyl-7,8-didehydro-6$\beta$-PGI$_1$, 11,15-bis(t-butyldimethylsilyl ether) as a colorless oil.

Silica gel TLC Rf is 0.50 in ethyl acetate and Skellysolve B (1:2). NMR absorptions are observed at 5.62-5.35, 5.11-4.59, 5.25-3.82, 3.71-3.31, 3.12-2.76, 2.63-1.07, 0.88, and 0.02$\delta$. Infrared absorptions are observed at 3400, 2920, 1650, 1460, 1345, 1245, 1210, 1080, 1000, 965, 890, 835, and 775 cm$^{-1}$.

J. 2-Decarboxy-2-hydroxymethyl-7,8-didehydro-6$\beta$-PGI$_1$, (formula XXXI) is then prepared by hydrolysis of the reaction product of Part I (0.252 g) using a 0.1 N hydrogen chloride solution in isopropanol (25 ml) at ambient temperature for 16 hr. The reaction mixture is then diluted with 200 ml of ethyl acetate, washed with brine, and dried over sodium sulphate. Concentration under reduced pressure yields 0.188 g of crude product as a yellow oil. High pressure liquid chromatography using acetone and methylene chloride (1:2) yields 0.084 g of pure formula XXXI prostacyclin intermediate.

Silica gel TLC Rf is 0.38 in acetone and methylene chloride (1:1). NMR absorptions are observed at 5.70-5.40, 5.15-4.68, 4.34-3.83, 3.73-3.38, 3.18-2.08, 1.85-1.04, and 0.88$\delta$. Infrared absorptions are observed at 3350, 2920, 1655, 1450, 1330, 1210, 1060, 960, 985, and 730 cm$^{-1}$. The mass spectrum for the trimethylsilyl derivative exhibits a high resolution peak at 554.3667 and other peaks at 539, 483, 464, 449, 438, 423, 395, 367, 348, and 173.

Example 2

7,8-Didehydro-6$\beta$-PGI$_1$ (Formula XLIII: g, R$_8$, Y$_1$, M$_1$, L$_1$, and R$_7$ are as defined in Example 1) and its methyl ester (Formula XLIV: X$_1$ is —COOCH$_3$). Refer to Chart C.

A. The Adams catalyst (platinum oxide 63 mq) is pre-reduced with hydrogen (1 atmosphere at ambient temperature) in 24 ml of water. After the introduction of a nitrogen atmosphere, sodium bicarbonate (1.56 g) is added and oxygen bubbled directly into the reaction mixture for 10 min. Thereupon a solution of the reaction product of Example 1 (63 mg) and 7 ml of acetone is added. The resulting mixture is then placed in an oil bath at 55°-57° C. and oxygen bubbled into the resulting, magnetically stirred suspension for 2.5 hr. The reaction mixture is then cooled, acidified with 6 ml of 2 N potassium bisulfate and filtered through diatomaceous earth. The filtrate is then diluted with 400 ml of ethyl acetate and the aqueous layer separated. The resulted ethyl acetate solution is then washed with 20 ml of brine and the brine solution back-extracted with ethyl acetate. The combined organic extract is then dried over sodium sulphate and concentrated under reduced pressure to yield 66 mg of crude formula XLIII oil: 7,8-didehydro-6$\beta$-PGI$_1$. High pressure liquid chromatography with ethyl acetate and acetic acid (95.5:0.5) yields 50 mg of pure product. Silica gel TLC Rf is 0.9 in the A-IX solvent system. NMR absorptions are observed at 5.69-5.45, 5.23-4.45, 4.45-3.90, 3.18-2.89, 2.65-2.01-1.05, and 0.88$\delta$. Infrared absorptions are observed at 3350, 2950, 1720, 1460, 1330, 1220, 1140, 1065, and 970 cm$^{-1}$.

The mass spectrum for the trimethylsilyl derivative exhibits a high resolution peak at 568.3404 and other peaks at 553, 452, 437, 381, 362, 279, and 173.

B. Treatment of the reaction product of Part A above (0.17 g) in diethyl ether and methanol (20:1) with excess ethereal diazomethane yields (after high pressure liquid chromatography with acetone and methylene chloride, 1:5) 126 mg of pure title 7,8-didehydro-6$\beta$-PGI$_1$, methyl ester. Silica gel TLC Rf is 0.33 in the A-IX solvent system and 0.41 in acetone and dichloromethane (1:2). NMR absorptions are observed at 5.70, 5.40, 5.28, 4.67, 4.44-4.78, 3.65, 2.65-2.08, 1.97-1.07, and 0.88$\delta$. Infrared absorptions are observed at 3400, 2950, 1740, 1440, 1220, 1065, and 970 cm$^{-1}$. The mass spectrum for the trimethylsilyl derivative exhibits a high resolution peak at 510.3183 and other peaks at 485, 479, 420, 394, 389, 323, 305, 304, 295, 294, and 173.

Example 3

7,8-Didehydro-6α-PGI$_1$ and its methyl ester Refer to Charts B and C.

A. The reaction product of Example 1, Part B, 3α,5α-dihydroxy-2β-(3α-hydroxy-trans-1-octenyl)-1α-cyclopentanephenylseledinyl acetic acid, γ-lactone, bis(t-butyldimethylsilyl ether), 4.0 g, is reacted with 4.1 ml of 1.5 M diisobutyl aluminum hydride according to the procedure of Example 1, Part E, to yield 3.54 g of the formula XXXII compound, 3α,5α-dihydroxy-2β-(3α-hydroxy-trans-octenyl)-1α-cyclopentanephenyl-selenidylacetic acid, γ-lactol, bis(t-butyldimethylsilyl ether).

B. The reaction product of Part A (2.54 g) is reacted with 0.467 g of the Grignard reagent prepared in Example 1, Part F, according to the procedure of Example 1, Part F, to yield 1.23 g of the formula XXXIII compound, 2-decarboxy-2-methylene-6-hydroxy-7-phenylseledinyl-PGF$_{1\alpha}$, 11,15-bis(t-butyldimethylsilyl ether).

C. The reaction product of Part B, (1.27 g) in triethylamine (0.302 g) and dichloromethane is reacted with 0.301 g of methylsulfonyl chloride according to the procedure of Example 1, Part G, to yield 31 mg of formula XXXIV product, 2-decarboxy-2-methylene-7β-phenylselenidyl-6α-PGI$_1$, bis(t-butyldimethylsilyl ether). Mass spectrum exhibits a weak molecular ion at 622, a demethylated high resolution peak at 607.4406 and other ions at 565, 551, 475, 401, and 215.

D. The reaction product of Part C (0.153 g) is reacted with 1.30 ml of a 0.5 M 9-BBN solution in tetrahydrofuran and 3N sodium hydroxide and 10% hydrogen peroxide according to the procedure of Example 1, Part I, to yield 83 mg of the primary alcohol corresponding to the formula XXXIV terminal olefin, 2-decarboxy-2-hydroxymethyl-7β-phenylseledinyl-6α-PGI$_1$, bis(t-butyldimethylsilyl ether). The mass spectrum exhibits weak molecular and demethylated molecular ions at 796 and 781 and a debutylated high resolution peak at 739.3486. Other mass spectral peaks are observed at 725, 664, 639, 607, 581, 480, and 215.

E. The reaction product of Part D (0.369 g) is dehydrophenylselenidylated according to the procedure of Example 1, Part C, yielding 47 mg of 2-decarboxy-2-hydroxymethyl-7,8-didehydro-6α-PGI$_1$, 11,15-bis(t-butyldimethylsilyl ether), a formula XXXV compound.

F. The reaction product of Part E (0.089 g) is desilylated according to the procedure of Example 1, Part J, yielding 39 mg of the formula XLII compound, 2-decarboxy-2-hydroxymethyl-7,8-didehydro-6α-PGI$_7$.

G. The reaction product of Part F (0.039 g) is oxidized to the corresponding carboxylic acid according to the procedure of Example 2, Part A, yielding 21 mg of 7,8-didehydro-6α-PGI$_1$. The high resolution mass spectrum exhibits a demethylated molecular ion at 553.3176.

H. The reaction product of Part G (0.002 g) is esterified according to the procedure of Example 2, Part B, yielding 7,8-didehydro-6α-PGI$_1$, methyl ester, a formula XLIV compound. The high resolution mass spectrum of the trimethylsilyl derivative exhibits a high resolution peak at 570.3173.

EXAMPLE 4

7,8-Didehydro-6β-PGI$_1$, p-hydroxybenzaldehyde semicarbazone ester (Formula IX: X$_1$ is

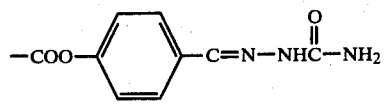

and g, R$_8$, L$_1$, M$_1$, R$_7$ and Y$_1$ are as defined in Example 1).

A solution of 1.0 g of 7,8-didehydro-6β-PGI$_1$ in 45 ml of dry acetone is cooled to 0° C. and treated dropwise with 0.51 ml of triethylamine. Thereafter 0.48 ml of isobutylchloroformate is added. This mixture is stirred for 10 min after which a triethylamine hydrochloride precipitate forms. A solution of 1.32 g of p-hydroxybenzaldehyde semicarbazone in 13 ml of pyridine is then added and the mixture allowed to warm to 25° C. This mixture is then stirred for 60 min and thereafter concentrated under reduced pressure. The residue is then dissolved in ethyl acetate and filtered. The filter cake is then washed with ethyl acetate and the combined filtrate is evaporated and chromatographed on 200 g of silica gel packed with 5% isopropanol and hexane. Eluting with 10% isopropanol and hexane yields pure product which is then rechromatographed with tetrahydrofuran. Thereupon pure title product is obtained.

EXAMPLE 5

7,8-Didehydro-6β-PGI$_1$, amide (Formula I: X$_1$ is —CONH$_2$, and g, R$_8$, Y$_1$, M$_1$, L$_1$, and R$_7$ are as defined in Example 1).

A solution of 393 mg of 7,8-didehydro-6β-PGI$_1$ and 5 ml of acetone is treated with 0.14 ml of triethylamine. This mixture is then cooled under a nitrogen atmosphere to −10° C. and treated with 0.13 ml of isobutylchloroformate. To this mixture is then added after 10 min at −10° C. 5 ml of acetonitrile saturated with ammonia. The resulting mixture is then warmed to 25° C. and stirred for 15 min. Following the removal of solvents under reduced pressure, the residue is diluted with brine and extracted with ethyl acetate. The ethyl acetate extracts are then washed with aqueous sodium bicarbonate and brine, dried over magnesium sulfate, and evaporated under reduced pressure to yield crude title product. This crude product is then chromatographed on 75 g of acid-washed silica gel packed with ethyl acetate. Eluting with ethyl acetate yields pure title product.

EXAMPLE 6

7,8-Didehydro-6β-PGI$_1$, p-carboxyanilide (Formula IX: X$_1$ is

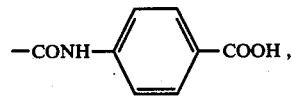

g, R$_8$, Y$_1$, M$_1$, L$_1$, and R$_7$ are as defined in Example 1).

To a solution of 393 mg of 7,8-didehydro-6β-PGI$_1$ at −10° C. in 5 ml of acetone is added 0.14 ml of triethylamine, followed by addition of 0.13 ml of isobutylchloroformate. The resulting mixture is then stirred at −10° C. for 10 min and thereafter treated with a mixture of 250 mg of p-amino-benzoic acid, 0.2 ml of triethylamine, and 5 ml of acetone. The resulting mixture is then warmed to 25° C. and stirred for 20 min. Thereafter the stirred mixture is poured into cold dilute aqueous sodium bisulfate and extracted with ethyl acetate. The organic extracts are then washed with brine, dried over magnesium sulfate and evaporated to yield crude product. This crude product is then chromatographed on 75 g of acid-washed silica gel packed with 40% ethyl acetate in hexane. Eluting with 40–70% ethyl acetate in hexane yields pure title product.

EXAMPLE 7

7,8-Didehydro-6$\beta$-PGI$_1$, methylsulfonylamide (Formula IX: X$_1$ is —CONHSO$_2$CH$_3$, g, R$_8$, Y$_1$, M$_1$, L$_1$, and R$_7$ are as defined in Example 1).

To a stirred solution of 480 mg of 7,8-didehydro-6$\beta$-PGI$_1$ in 6.0 ml of dimethylformamide and 0.142 g of triethylamine is added with stirring followed by addition of 0.19 g of isobutyl chloroformate. This mixture is then stirred at 0° C. for 25 min at which time 0.685 g of methylsulfonamide sodium salt (prepared by adding 1.33 ml of 4.4 N methanolic sodium methoxide to a solution of 0.604 g of methanesulfonamide in 2.0 ml of methanol, concentrating the mixture under reduced pressure, adding benzene to the residue, and again concentrating the mixture under reduced pressure). Thereafter 1.25 ml of hexamethylphosforamide is added and the mixture stirred at ambient temperature for 16 hr. Acidification with cold dilute hydrochloric acid is followed by extraction with ethyl acetate. The organic extract is then washed with water, brine and dried over magnesium sulfate. Concentration at reduced pressure yields a residue which is chromatographed on a 100 g column of silica gel packed with 10% methanol in methylene chloride. Eluting with 7.5% methanol in methylene chloride yields crude product which is then diluted with ether, washed with cold dilute hydrochloric acid, water, and saturated brine. Drying over magnesium sulfate and concentrating under reduced pressure yields a residue of pure title product.

Following the procedure of Example 4, but employing the respective phenols corresponding to the various phenyl esters described above, there are prepared the various 7,8-didehydro-PGI$_1$, phenyl and substituted phenyl esters described herein.

Following the procedure of Example 5, but employing amines corresponding to each of the various amido and cycloamido groups described above in place of ammonia, there are prepared the various amido and cycloamido derivatives of 7,8-didehydro-PGI$_1$ analogs described herein.

EXAMPLE 8

7,8-Didehydro-6$\beta$-PGI$_1$, sodium salt (Formula IX: X$_1$ is —COO$^-$Na$^+$, g, R$_8$, Y$_1$, M$_1$, L$_1$, and R$_7$ are as defined in Example 1).

A solution of 383 mg of 7,8-didehydro-6$\beta$-PGI$_1$ in 8.5 ml of methanol under a nitrogen atmosphere are treated at 25° C. with a single equivalent (8.8 ml) of 0.1 N sodium methoxide in methanol for 5 hr. The resulting solution is then concentrated under reduced pressure (removing the methyl acetate byproduct), then redissolved in 8.5 ml of methanol and 1.5 ml of water. This solution is then stirred for 12 hr under a nitrogen atmosphere whereupon 10 ml of water is added and the methanol removed under reduced pressure. The resulting aqueous solution is then lyophilized yielding a residue of pure title product.

EXAMPLE 9

7,8-Didehydro-6$\beta$-PGI$_1$, tris(hydroxymethyl) aminomethane salt

An ethereal solution of 7,8-didehydro-6$\beta$-PGI$_1$ is combined with stirring with a solution of tris(hydroxymethyl) aminomethane, containing exactly one equivalent of the amine base. The resulting aqueous solution, containing the title salt, is then purified in accordance with the isolation procedure of Example 8, thereby yielding pure title product.

Following the procedure of the above examples, but employing the appropriate bicyclic lactone starting material, there are prepared 7,8-didehydro-6$\alpha$-or 6$\beta$-PGI$_1$-type compounds;

11-deoxy-7,8-didehydro-6$\alpha$- or 6$\beta$-PGI$_1$-type compounds;

11-deoxy-11-hydroxymethyl-7,8-didehydro-6$\alpha$- or 6$\beta$-PGI$_1$-type compounds; as free acids, amides, esters, or pharmacologically acceptable salts which exhibit the following side chain substituents:

15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-13,14-didehydro-;
16,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;

17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetraor-13,14-didehydro-;
16-(m-fluorophenyl)-17,18,19,20-tetranor-13,14-didehydro-;
16-(p-fluorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-,
16-(m-chlorophenyl)-17,18,19,20-tetranor-13,14-didehydro-;
16-(p-fluorophenyl)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-chlorophenoxy)-17,18,19,20-tetranor-13-cis-;
16-Phenoxy-18,19,20-trinor-13-cis-;
16-Methyl-16-phenoxy:18,19,20-trinor-13-cis-;
2a,2b-Dihomo-;
2a,2b-Dihomo-16-methyl-;
2a,2b-Dihomo-16,16-dimethyl-;
2a,2b-Dihomo-16-fluoro-;
2a,2b-Dihomo-16,16-difluoro-;
2a,2b-Dihomo-17-phenyl-18,19,20-trinor-;
2a,2b-Dihomo-17-(m-trifluoromethylphenyl)-18,19,20-trinor-;
2a,2b-Dihomo-17-(m-chlorophenyl)-18,19,20-trinor-;
2a,2b-Dihomo-17-(p-fluorophenyl)-18,19,20-trinor-;
2a,2b-Dihomo-16-methyl-17-phenyl-18,19,20-trinor-;
2a,2b-Dihomo-16,16-dimethyl-17-phenyl-18,19,20-trinor-;
2a,2b-Dihomo-16-fluoro-17-phenyl-18,19,20-trinor-;
2a,2b-Dihomo-16,16-difluoro-17-phenyl-18,19,20-trinor-;
2a,2b-Dihomo-16-phenyl-17,18,19,20-tetranor-;
2a,2b-Dihomo-16-(m-trifluoromethylphenyl)-17,18,19,20-tetranor-;
2a,2b-Dihomo-16-(m-chlorophenyl)-17,18,19,20-tetranor-;
2a,2b-Dihomo-16-(p-fluorophenyl)-17,18,19,20-tetranor-;
2a,2b-Dihomo-16-phenyl-18,19,20-trinor-;
2a,2b-Dihomo-16-methyl-16-phenyl-18,19,20-trinor-;
2a,2b-Dihomo-16-phenoxy-17,18,19,20-tetranor-;
2a,2b-Dihomo-16-(m-trifluoromethylphenoxy)-17,18,19,20-tetranor-;
2a,2b-Dihomo-16-(m-chlorophenoxy)-17,18,19,20-tetranor-;
2a,2b-Dihomo-16-(p-fluorophenoxy)-17,18,19,20-tetranor-;
2a,2b-Dihomo-16-phenoxy-18,19,20-trinor-;
2a,2b-Dihomo-16-methyl-16-phenoxy-18,19,20-trinor-;
2a,2b-Dihomo-16-methyl-13,14-didehydro-;
2a,2b-Dihomo-16,16-dimethyl-13,14-didehydro-;
2a,2b-Dihomo-16-fluoro-13,14-didehydro-;
2a,2b-Dihomo-16,16-difluoro-13,14-didehydro-;
2a,2b-Dihomo-17-phenyl-18,19,20-trinor-13,14-didehydro-;
2a,2b-Dihomo-17-(m-trifluoromethylphenyl)-18,19,20-trinor-13,14-didehydro-;

2a,2b-Dihomo-17-(m-chlorophenyl)-18,19,20-trinor-13,14-didehydro-;
2a,2b-Dihomo-17-(p-fluorophenyl)-18,19,20-trinor-13,14-didehydro-;
2a,2b-Dihomo-16-methyl-17-phenyl-18,19,20-trinor-13,14-didehydro-;
2a,2b-Dihomo-16,16-dimethyl-17-phenyl-18,19,20-trinor-13,14-didehydro-;
2a,2b-Dihomo-16-fluoro-17-phenyl-18,19,20-trinor-13,14-didehydro-;
2a,2b-dihomo-16,16-difluoro-17-phenyl-18,19,20-trinor-13,14-didehydro-;
2a,2b-Dihomo-16-phenyl-17,18,19,20-tetranor-13,14-didehydro-;
2a,2b-Dihomo-16-(m-trifluoromethylphenyl)-17,18,19,20-tetranor-13,14-didehdro-;
2a,2b-Dihomo-16-(m-chlorophenyl)-17,18,19,20-tetranor-13,14-didehydro-;
2a,2b-Dihomo-16-(p-fluorophenyl)-17,18,19,20-tetranor-13,14-didehydro-;
2a,2b-Dihomo-16-phenyl-18,19,20-trinor-13,14-didehydro-;
2a,2b-Dihomo-16-methyl-16-phenyl-18,19,20-trinor-13,14-didehydro-;
2a,2b-Dihomo-16-phenoxy-17,18,19,20-tetranor-13,14-didehydro-;
2a,2b-Dihomo-16-(m-trifluoromethylphenoxy)-17,18,19,20-tetranor-13,14-didehydro-;
2a,2b-Dihomo-16-(m-chlorophenoxy)-17,18,19,20-tetranor-13,14-didehydro-;
2a,2b-Dihomo-16-(p-fluorophenoxy)-17,18,19,20-tetranor-13,14-didehydro-;
2a,2b-Dihomo-16-phenoxy-18,19,20-trinor-13,14-didehydro-;
2a,2b-Dihomo-16-methyl-16-phenoxy-18,19,20-trinor-13,14-didehydro-;
;b 2a,2b-Dihomo-13,14-dihydro-;
2a,2b-Dihomo-16-methyl-13,14-dihydro-;
2a,2b-Dihomo-16,16-dimethyl-13,14-dihydro-;
2a,2b-Dihomo-16-fluoro-13,14-dihydro-;
2a,2b-Dihomo-16,16-Difluoro-13,14-dihydro-;
2a,2b-Dihomo-17-phenyl-18,19,20-trinor-13,14-dihydro-,
2a,2b-Dihomo-17-(m-trifluoromethylphenyl)-18,19,20-trinor-13,14-dihydro-;
2a,2b-Dihomo-17-(m-chlorophenyl)-18,19,20-trinor-13,14-dihydro-;
2a,2b-Dihomo-17-(p-fluorophenyl)-18,19,20-trinor-13,14-dihydro-;
2a,2b-Dihomo-16-methyl-17-phenyl-18,19,20-trinor-13,14-dihydro-;
2a,2b-Dihomo-16,16-dimethyl-17-phenyl-18,19,20-trinor-13,14-dihydro-;
2a,2b-Dihomo-16-fluoro-17-phenyl-18,19,20-trinor-13,14-dihydro-;
2a,2b-Dihomo-16,16-difluoro-17-phenyl-18,19,20-trinor-13,14-dihydro-;
2a,2b-Dihomo-16-phenyl-17,18,19,20-tetranor-13,14-dihydro-;
2a,2b-Dihomo-16-(m-trifluoromethylphenyl)-17,18,19,20-tetranor-13,14-dihydro-;
2a,2b-Dihomo-16-(m-chlorophenyl)-17,18,19,20-tetranor-13,14-dihydro-;
2a,2b-Dihomo-16-(p-fluorophenyl)-17,18,19,20-tetranor-13,14-dihydro-;
2a,2b-Dihomo-16-phenyl-18,19,20-trinor-13,14-dihydro-;
2a,2b-Dihomo-16-methyl-16-phenyl-18,19,20-trinor-13,14-dihydro-;
2a,2b-Dihomo-16-phenoxy-17,18,19,20-tetranor-13,14-dihydro-;
2a,2b-Dihomo-16-(m-trifluoromethylphenoxy)-17,18,19,20-tetranor-13,14-dihydro-;
2a,2b-Dihomo-16-(m-chlorophenoxy)-17,18,19,20-tetranor-13,14-dihydro-;
2a,2b-Dihomo-16-(p-fluorophenoxy)-17,18,19,20-tetranor-13,14-dihydro-;
2a,2b-Dihomo-16-methyl-16-phenoxy-18,19,20-trinor-13,14-dihydro-;
2a,2b-Dihomo-13-cis-;
2a,2b-Dihomo-16-methyl-13-cis-;
2a,2b-Dihomo-16,16-dimethyl-13cis-;
2a,2b-Dihomo-16-fluoro-13-cis-;
2a,2b-Dihomo-16,16-difluoro-13-cis-;
2a,2b-Dihomo-17-phenyl-18,19,20-trinor-13-cis-;
2a,2b-Dihomo-17-(m-trifluoromethylphenyl)-18,19,20-trinor-13-cis-;
2a,2b-Dihomo-17-(m-chlorophenyl)-18,19,20-trinor-13-cis-;
2a,2b-Dihomo-17-(m-fluorophenyl)-18,19,20-trinor-13-cis-;
2a,2b-Dihomo-16-methyl-17-phenyl-18,19,20-trinor-13-cis-;
2a,2b-Dihomo-16,16-dimethyl-17-phenyl-18,19,20-trinor-13-cis-;
2a,2b-Dihomo-16-fluoro-17-phenyl-18,19,20-trinor-13-cis-;
2a,2b-Dihomo-16,16-difluoro-17-phenyl-18,19,20-trinor-13-cis-;
2a,2b-Dihomo-16-phenyl-17,18,19,20-tetranor-13-cis-;
2a,2b-Dihomo-16-(m-trifluoromethylphenyl)-17,18,19,20-tetranor-13-cis-;
2a,2b-Dihomo-16-(m-chlorophenyl)-17,18,19,20-tetranor-13-cis-;
2a,2b-Dihomo-(p-fluorophenyl)-17,18,19,20-tetranor-13-cis-;
2a,2b-Dihomo-16-phenyl-18,19,20-trinor-13-cis-;
2a,2b-Dihomo-16-methyl-16-phenyl-18,19,20-trinor-13-cis-;
2a,2b-Dihomo-16-phenoxy-17,18,19,20-tetranor-13-cis-;
2a,2b-Dihomo-16-(m-trifluoromethylphenoxy)-17,18,19,20-tetranor-13-cis-;
2a,2b-Dihomo-16-(m-chlorophenoxy)-17,18,19,20-tetranor-13-cis-;
2a,2b-Dihomo-16-(p-fluorophenoxy)-17,18,19,20-tetranor-13-cis-;
2a,2b-Dihomo-16-phenoxy-18,19,20-trinor-13-cis-; and
2a,2b-Dihomo-16-methyl-16-phenoxy-18,19,20-trinor-13-cis-.

I claim:
1. A prostacyclin intermediate of the formula

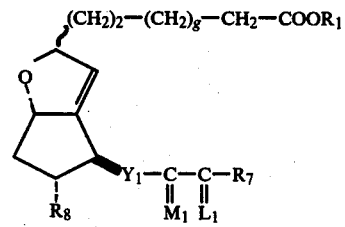

wherein g is the integer one, 2, or 3;
wherein $R_8$ is hydrogen, hydroxy, or hydroxymethyl;
wherein $Y_1$ is
(1) trans—CH=CH—,
(2) cis—CH=CH—,
(3) —CH$_2$CH$_2$—, or
(4) —C≡C—;
wherein $M_1$ is

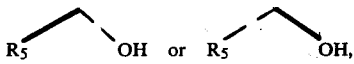

wherein $R_5$ is hydrogen or methyl; wherein $L_1$ is

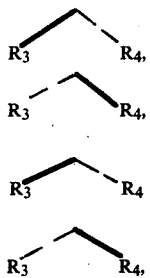

or a mixture of and wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is

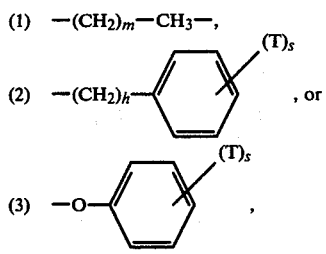

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl; and
wherein $R_1$ is hydrogen, alkyl of one to 12 carbon atoms, inclusive, cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

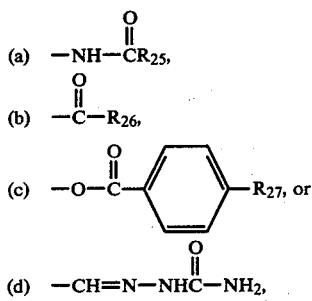

wherein $R_{25}$ is methyl, phenyl, acetamidophenyl, benzamidophenyl, or —NH$_2$; $R_{26}$ is methyl, phenyl, —NH$_2$, or methoxy; and $R_{27}$ is hydrogen or acetamido, inclusive, phenacyl, i.e.,

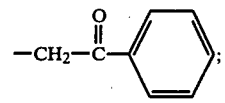

or phenacyl substituted in the para position by chloro, bromo, phenyl, or benzamido; or a pharmacologically acceptable cation.

2. A prostacyclin analog according to claim 1, wherein $R_8$ is hydroxymethyl.

3. 11-Deoxy-11α-hydroxymethyl-7,8-didehydro-6α- or 6β-PGI$_1$, prostacyclin analog according to claim 2.

4. A prostacyclin analog according to claim 1, wherein $R_8$ is hydrogen.

5. 11-Deoxy-7,8-didehydro-6α- or 6β-PGI$_1$, prostacyclin analogs according to claim 4.

6. A prostacyclin analog according to claim 1, wherein $R_8$ is hydroxy.

7. A prostacyclin analog according to claim 6, wherein $Y_1$ is —C≡C—.

8. 7,8,13,14-Tetrahydro-6α- or 6β-PGI$_1$, prostacyclin analogs according to claim 7.

9. 15-Methyl-7,8,13,14-tetradehydro-6α- or 6β-PGI$_1$, prostacyclin analogs according to claim 7.

10. 16,16-Dimethyl-7,8,13,14-tetradehydro-6α- or 6β-PGI$_1$, prostacyclin analogs according to claim 7.

11. 2a,2b-Dihomo-15-methyl-7,8,13,14-tetradehydro-6α- or 6β-PGI$_1$, prostacyclin analogs according to claim 7.

12. A prostacyclin analog according to claim 6, wherein $Y_1$ is cis—CH=CH—.

13. cis-13-7,8-Didehydro-6α- or 6β-PGI$_1$, prostacyclin analogs according to claim 12.

14. A prostacyclin analog according to claim 6, wherein $Y_1$ is —CH$_2$CH$_2$—.

15. 13,14-Dihydro-7,8-didehydro-6α- or 6β-PGI$_1$, prostacyclin analogs according to claim 14.

16. 13,14-Dihydro-15-methyl-7,8-didehydro-6α- or 6β-PGI$_1$, prostacyclin analogs according to claim 14.

17. 13,14-Dihydro-16,16-dimethyl-7,8-didehydro-6α- or 6β-PGI$_1$, prostacyclin analogs according to claim 14.

18. 13,14-Dihydro-2a,2b-dihomo-15-methyl-7,8-didehydro-6α- or 6β-PGI$_1$, prostacyclin analogs according to claim 14.

19. 13,14-Dihydro-2a,2b-dihomo-16,16-difluoro-7,8-didehydro-6α- or 6β-PGI$_1$, prostacyclin analogs according to claim 14.

20. A prostacyclin analog according to claim 6, wherein $Y_1$ is trans—CH=CH—.

21. A prostacyclin analog according to claim 20, wherein g is 3.

22. 2a,2b-Dihomo-15-methyl-7,8-didehydro-6α- or 6β-PGI$_1$, prostacyclin analogs according to claim 21.

23. 2a,2b-Dihomo-16,16-dimethyl-7,8-didehydro-6α- or 6β-PGI$_1$, prostacyclin analogs according to claim 21.

24. 2a,2b-Dihomo-16,16-difluoro-7,8-didehydro-6α- or 6β-PGI$_1$, prostacyclin analogs according to claim 21.

25. A prostacyclin analog according to claim 20, wherein g is one.

26. A prostacyclin analog according to claim 25, which is in the alpha configuration for the C-6 side chain.

27. A prostacyclin analog according to claim 26, wherein $R_7$ is

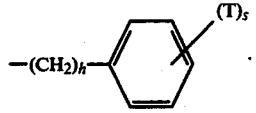

28. 17-Phenyl-18,19,20-trinor-7,8-didehydro-6α-PGI$_1$, a prostacyclin analog according to claim 27.

29. A prostacyclin analog according to claim 26, wherein R$_7$ is

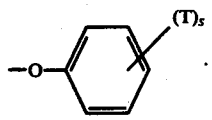

30. 16-Phenoxy-17,18,19,20-tetranor-7,8-didehydro-6α-PGI$_1$, a prostacyclin analog according to claim 29.

31. A prostacyclin analog according to claim 26, wherein R$_7$ is —(CH$_2$)$_m$—CH$_3$.

32. A prostacyclin analog according to claim 31, wherein m is 3.

33. A prostacyclin analog according to claim 32, wherein R$_5$ is methyl.

34. 15-Methyl-7,8-didehydro-6α-PGI$_1$, a prostacyclin analog according to claim 33.

35. A prostacyclin analog according to claim 32, wherein R$_5$ is hydrogen.

36. A prostacyclin analog according to claim 35, wherein at least one of R$_3$ and R$_4$ is fluoro.

37. 16,16-Difluoro-7,8-didehydro-6α-PGI$_1$, a prostacyclin analog according to claim 36.

38. A prostacyclin analog according to claim 35, wherein at least one of R$_3$ and R$_4$ is methyl.

39. 16,16-Dimethyl-7,8-didehydro-6α-PGI$_1$, a prostacyclin analog according to claim 38.

40. A prostacyclin analog according to claim 35, wherein R$_3$ and R$_4$ are both hydrogen.

41. 7,8-Didehydro-6α-PGI$_1$, methyl ester, a prostacyclin analog according to claim 40.

42. 7,8-Didehydro-6α-PGI$_1$, tris(hydroxymethyl)aminomethane salt, a prostacyclin analog according to claim 40.

43. 7,8-Didehydro-6α-PGI$_1$, adamantanamine salt, a prostacyclin analog according to claim 40.

44. 7,8-Didehydro-6α-PGI$_1$, a prostacyclin analog according to claim 40.

45. A prostacyclin analog according to claim 25, which is in the beta configuration for the C-6 side chain.

46. A prostacyclin analog according to claim 45, wherein R$_7$ is

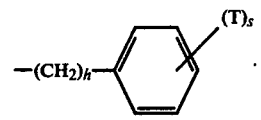

47. 17-Phenyl-18,19,20-trinor-7,8-didehydro-6β-PGI$_1$, a prostacyclin analog according to claim 46.

48. A prostacyclin analog according to claim 45, wherein R$_7$ is

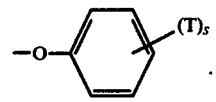

49. 16-Phenoxy-17,18,19,20-tetranor-7,8-didehydro-6β-PGI$_1$, a prostacyclin analog according to claim 48.

50. A prostacyclin analog according to claim 45, wherein R$_7$ is —(CH$_2$)$_m$—CH$_3$.

51. A prostacyclin analog according to claim 50, wherein m is 3.

52. A prostacyclin analog according to claim 51, wherein R$_5$ is methyl.

53. 15-Methyl-7,8-didehydro-6β-PGI$_1$, a prostacyclin analog according to claim 52.

54. A prostacyclin analog according to claim 51, wherein R$_5$ is hydrogen.

55. A prostacyclin analog according to claim 54, wherein at least one of R$_3$ and R$_4$ is fluoro.

56. 16,16-Difluoro-7,8-didehydro-6β-PGI$_1$, a prostacyclin analog according to claim 55.

57. A prostacyclin analog according to claim 54, wherein at least one of R$_3$ and R$_4$ is methyl.

58. 16,16-Dimethyl-7,8-didehydro-6β-PGI$_1$, a prostacyclin analog according to claim 57.

59. A prostacyclin analog according to claim 54, wherein R$_3$ and R$_4$ are both hydrogen.

60. 7,8-Didehydro-6β-PGI$_1$, methyl ester, a prostacyclin analog according to claim 59.

61. 7,8-Didehydro-6β-PGI$_1$, tris(hydroxymethyl)aminomethane salt, a prostacyclin analog according to claim 59.

62. 7,8-Didehydro-6β-PGI$_1$, adamantanamine salt, a prostacyclin analog according to claim 59.

63. 7,8-Didehydro-6β-PGI$_1$, a prostacyclin analog according to claim 59.

* * * * *

UNITED STATES PATENT OFFICE
CERTIFICATE OF CORRECTION

Patent No. 4,151,351             Dated   24 April 1979

Inventor(s)   John C. Sih

It is certified that error appears in the above-identified patent and that said Letters Patent are hereby corrected as shown below:

Column 20, line 62, "amids or cycloamido" should read -- amido or cycloamido --;
Column 22, line 62, "bis(t-butyleimthylsilyl ether)" should read -- bis(t-butyldimethylsilyl ether) --;
Column 23, line 21, "bis(t-butyldimethylsill ether)" should read -- bis(t-butyldimethylsilyl ether) --;
Column 26, line 25, "63 mq" should read -- 63 mg --; line 49, "2.65-2.01-1.05," should read -- 2.65-2.01, 2.01-1.05, --
Column 31, line 12, "tetraor-" should read -- tetranor- --.

Signed and Sealed this

Eleventh Day of August 1981

[SEAL]

Attest:

GERALD J. MOSSINGHOFF

Attesting Officer           Commissioner of Patents and Trademarks